(12) United States Patent
Nelson

(10) Patent No.: US 11,607,566 B1
(45) Date of Patent: Mar. 21, 2023

(54) AUTOMATED 3D DOSIMETRY

(71) Applicant: Brett K Nelson, Scotts Valley, CA (US)

(72) Inventor: Brett K Nelson, Scotts Valley, CA (US)

( * ) Notice: Subject to any disclaimer, the term of this patent is extended or adjusted under 35 U.S.C. 154(b) by 0 days.

(21) Appl. No.: 16/904,133

(22) Filed: Jun. 17, 2020

Related U.S. Application Data

(63) Continuation-in-part of application No. 16/698,610, filed on Nov. 27, 2019, now abandoned.

(51) Int. Cl.
*A61N 5/10* (2006.01)
*G01T 1/02* (2006.01)

(52) U.S. Cl.
CPC ............ *A61N 5/1075* (2013.01); *G01T 1/023* (2013.01); *A61N 2005/1072* (2013.01); *A61N 2005/1076* (2013.01)

(58) Field of Classification Search
CPC .......... A61N 5/1075; A61N 2005/1072; A61N 2005/1076; G01T 1/023
See application file for complete search history.

(56) References Cited

U.S. PATENT DOCUMENTS

| | | | | |
|---|---|---|---|---|
| 3,536,914 A * | 10/1970 | Chapman | ................ | G01T 1/203 250/367 |
| 4,788,436 A * | 11/1988 | Koechner | ............... | G01T 1/201 250/227.23 |
| 5,132,543 A * | 7/1992 | Valentine | ................. | G01T 1/18 250/374 |
| 5,856,673 A * | 1/1999 | Ikegami | .................. | G01T 1/202 250/368 |
| 7,636,419 B1 * | 12/2009 | Nelson | ................. | A61N 5/1048 250/363.01 |
| 9,625,583 B2 | 4/2017 | Beddar | | |
| 2002/0121604 A1 * | 9/2002 | Katagiri | ................ | G01T 1/1644 250/368 |
| 2003/0150983 A1 * | 8/2003 | Nishizawa | ........... | A61N 5/1048 250/252.1 |
| 2003/0212302 A1 * | 11/2003 | Rozenfeld | ............ | A61N 5/1007 600/1 |
| 2004/0051045 A1 * | 3/2004 | Jones | ...................... | G01T 1/202 250/368 |
| 2008/0029709 A1 * | 2/2008 | Yeo | ....................... | A61N 5/1048 250/374 |

(Continued)

OTHER PUBLICATIONS

Kim, Yewon et al., "Plastic Scintillator for Radiation Dosimetry", Radiation Protection Dosimetry 170(1-4), pp. 187-190 (Year: 2016).*

*Primary Examiner* — Blake C Riddick
(74) *Attorney, Agent, or Firm* — Useful Arts IP

(57) ABSTRACT

An improved hodoscope radiation detector includes a cone filled with a plastic medium that is closer to the density of water ("tissue equivalent") than air. The medium may have the following properties:
1) Highly transparent with little optical distortion
2) Produces light along the path of incident radiation (x-rays, protons, and ions of heavier weight like carbon, helium, etc.—also called hadrons)
3) Moldable and/or machinable (i.e., not a hard crystal)
4) Homogeneous—evenly distributed density.
This medium can fill the cone completely or only a section of the cone (i.e., frustum) or a subsection of the cone such as a cylinder.

15 Claims, 7 Drawing Sheets

(56) References Cited

U.S. PATENT DOCUMENTS

| | | | |
|---|---|---|---|
| 2009/0014665 A1* | 1/2009 | Fleming | G01T 1/023 250/484.5 |
| 2011/0101228 A1* | 5/2011 | Hamby | G01T 1/008 250/362 |
| 2012/0168630 A1* | 7/2012 | Beddar | G01T 1/04 250/362 |
| 2014/0051968 A1* | 2/2014 | Isham | A61N 5/10 600/407 |
| 2015/0157879 A1* | 6/2015 | Wu | A61N 5/1067 378/8 |
| 2016/0001094 A1* | 1/2016 | Isham | G01T 1/02 600/1 |
| 2016/0041270 A1* | 2/2016 | Dai | G01T 1/023 250/361 R |
| 2018/0154182 A1* | 6/2018 | Shin | A61N 5/1071 |
| 2020/0124744 A1* | 4/2020 | Leder | G01T 1/023 |
| 2020/0268475 A1* | 8/2020 | Adler, Jr. | A61N 5/1049 |

* cited by examiner

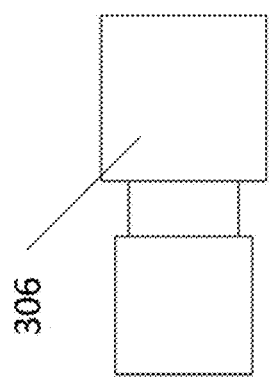
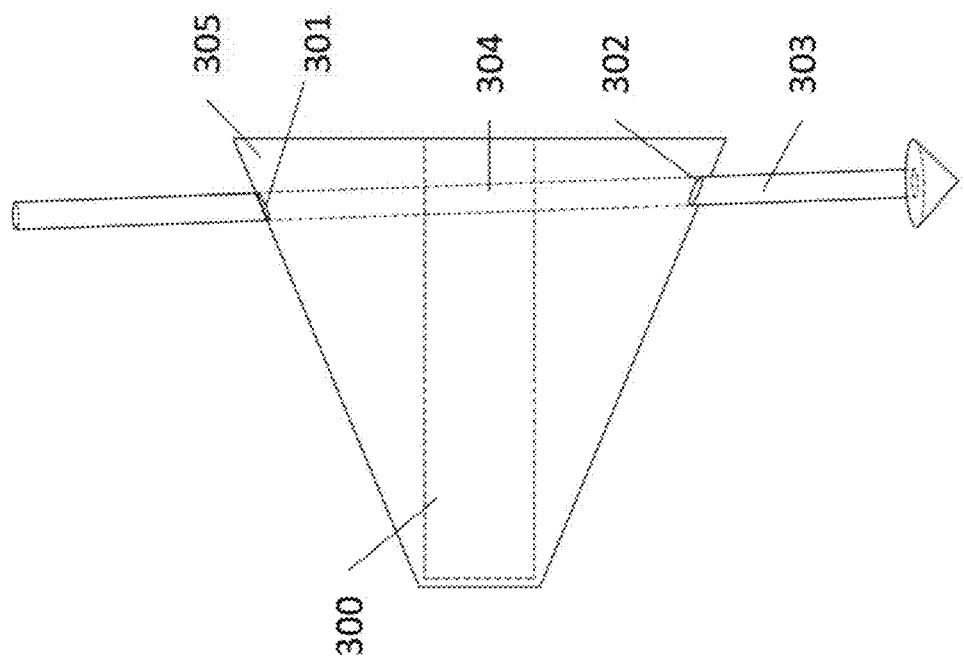
Fig.3

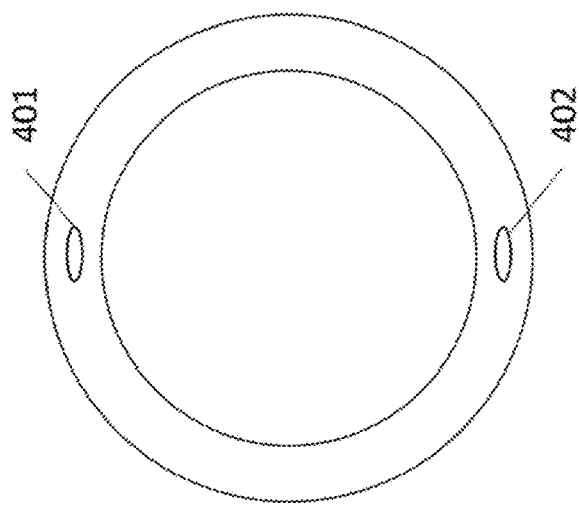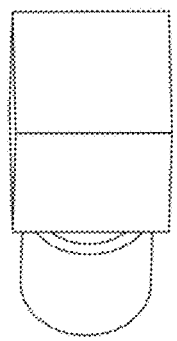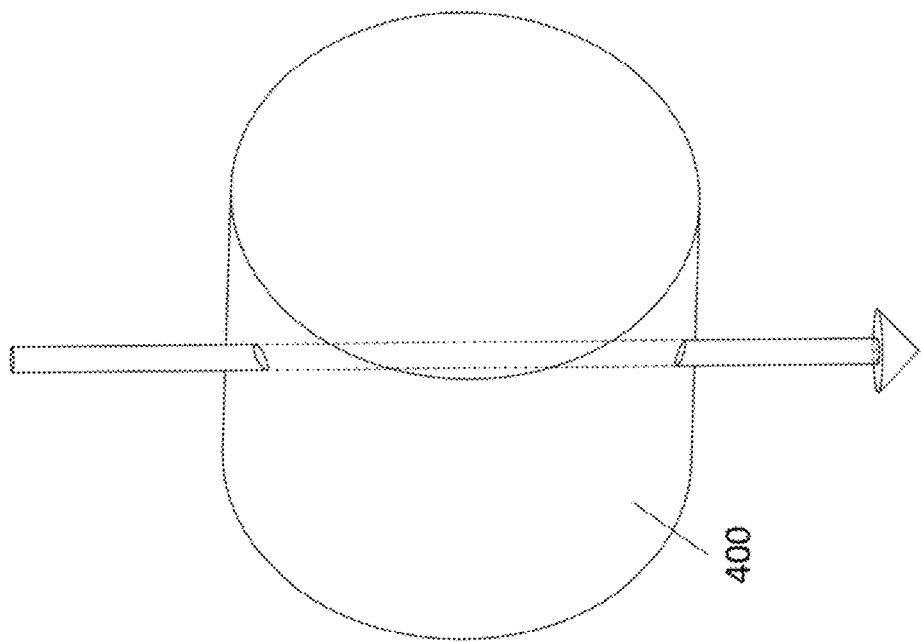
Fig.4

AUTOMATED 3D DOSIMETRY

BACKGROUND

A hodoscope is an instrument for observing the paths of x-rays and subatomic particles. Hodoscopes are particularly useful in the medical field, in connection with radiation therapy. One hodoscope is described in U.S. Pat. No. 7,636,419 by Nelson ("the Nelson patent"), incorporated herein by reference. In the Nelson patent, the imaging cone described has a scintillator viewed by a single camera. In practice, the cone is hollow and filled with air to offer minimum optical distortion of the entry and exit spots of light produced on the inside of the cone by the x-rays, proton, or heavy ion beams passing through the cone.

BRIEF DESCRIPTION OF THE DRAWING FIGURES

The present invention may be understood from the following description in conjunction with the appended drawing figures. In the drawing:

FIG. 3 is a section view of the hodoscope of FIG. 2.

FIG. 4 is a view showing an example camera image using the hodoscope of FIG. 2 and FIG. 3.

DESCRIPTION

Summary

An improved hodoscope radiation detector includes a cone filled with a plastic medium that is closer to the density of water ("tissue equivalent") than air. The medium may have the following properties:

1) Highly transparent with little optical distortion
2) Produces light along the path of incident radiation (x-rays, protons, and ions of heavier weight like carbon, helium, etc.—also called hadrons)
3) Moldable and/or machinable (i.e., not a hard crystal)
4) Homogeneous—evenly distributed density.

This medium can fill the cone completely or only a section of the cone (i.e., frustum) or a subsection of the cone approximating the shape of a cylinder. Because 3D dosimetry information can be directly observed (instead of being derived from the attributes of entry and exit spots) it is less influenced by camera electronics and closer to the reality of what is happening within the patient during radiosurgery or proton/ion therapy.

DETAILED DESCRIPTION

Figure 1:
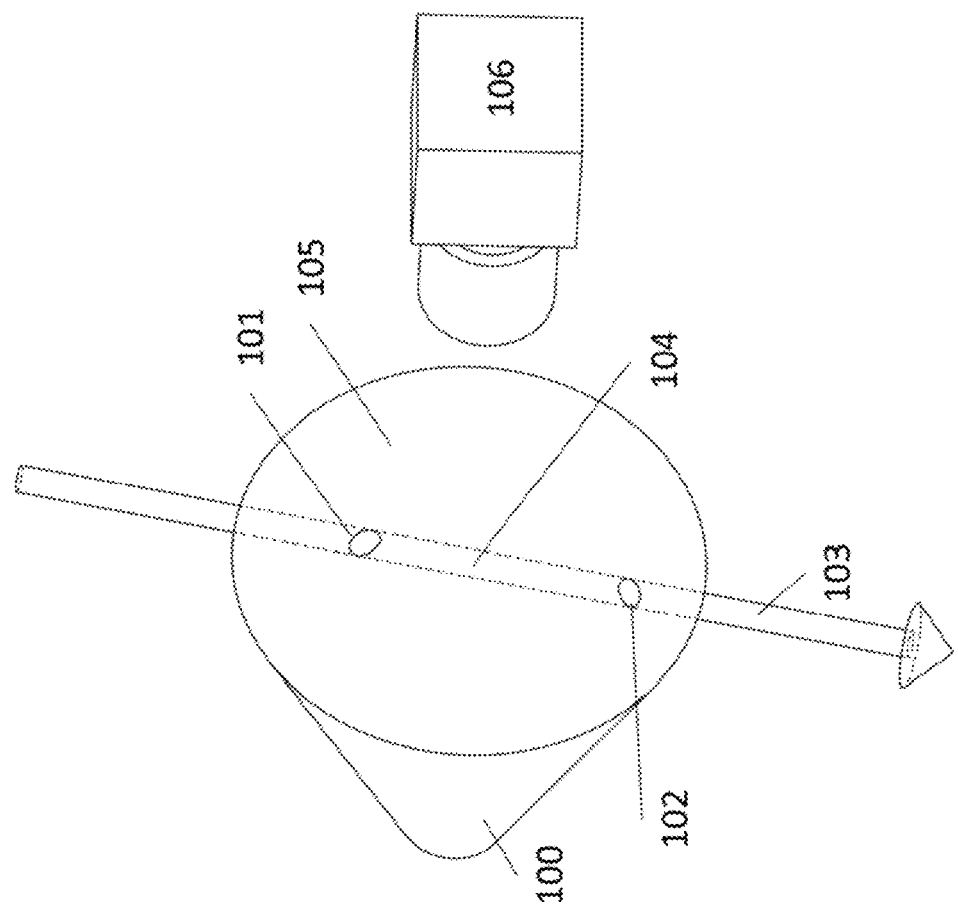
FIG. 1 is a simplified diagram of a hodoscope.

Referring now to FIG. 1, a simplified view of an improved hodoscope is shown. An imaging cone 100 is filled, wholly or partly, with a tissue-equivalent medium 105. The medium may be a plastic scintillating material, for example polyvinyltoulene. One suitable plastic is known by the designation Bicron BC-412A. A high speed digital camera 106 views the inside of the imaging cone and may be co-axial with a center axis of the cone, as shown in further detail FIG. 3. A particle beam traverses the imaging cone, producing a spot 101 at a point of entry and a spot 102 at a point of exit. A beam segment 104 is interior to the cone, and a beam segment 103 is exterior to the cone.

The 3D path of the radiation can be inferred from the position and shape of entry/exit spots, and by the additional light generated as the radiation beam passes through the plastic. This additional light provides important additional information, for example:

1) The direct path of the radiation as illuminated in the plastic medium can be averaged over time to closely approximate the 3D dose that was originally defined in a treatment plan. This is especially useful for protons and heavier ions (hadrons) that need a tissue/water-equivalent medium to slow down and deliver energy to the prescribed 3D treatment volume.

2) For X-rays, the depth/dose characteristics of the beam can be directly observed and measured.

3) For protons and heavy ions, the range of the ions (which is a function of original energy (50-500 MeV typically) can be directly observed and measured. The peak of the energy deposition curve is called the Bragg peak and can be observed and measured in the plastic scintillator.

For modern digital cameras and lenses, the angle of the imaging cone can be very small without adversely affecting results of the present techniques. In fact, a cylinder may be considered a section of an infinitely long cone as long as the lens views the inside of the cylinder.

Figure 2:
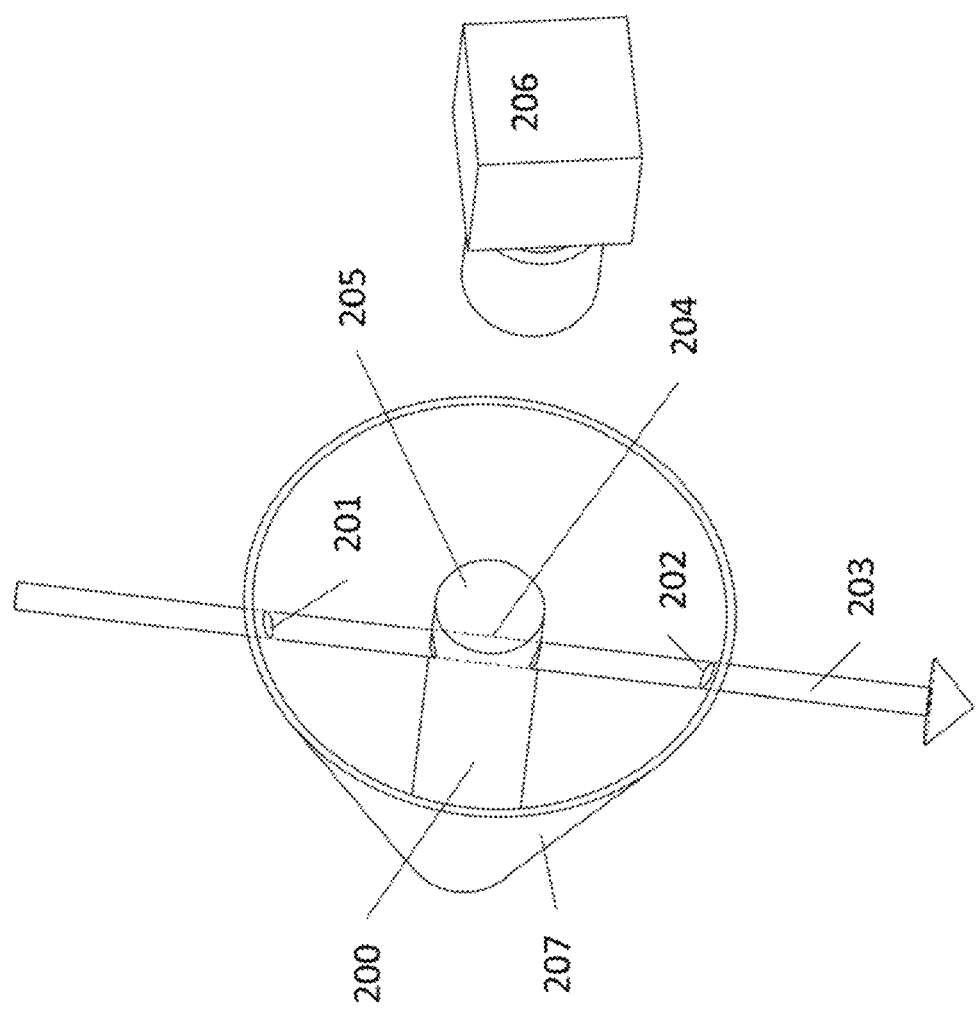
FIG. 2 is a diagram of a variation of the hodoscope of FIG. 1.

A hodoscope like that of FIG. 1 is shown in FIG. 2, but in which the imaging cone 207 is filled only partially, within the volume of a cone 200.

A sectional view of the hodoscope of FIG. 2 is shown in FIG. 3. An example showing a camera view of a beam using the hodoscope of FIG. 2 and FIG. 3 is shown in FIG. 4.

Using the hodoscopes of FIGS. 1-3, complete arc-style radiation treatments can be captured and measured dosimetrically for, X-rays, ion beams or other types of beams.

As illustrated in FIG. 1, a radiation beam will, in many cases, produce an entry and exit spot of visible light as it passes through the scintillator affixed to the interior of the imaging cone. For some ion beams, however, beams entering into an imaging cone filled with transparent plastic scintillator (or liquid scintillator), the entry spot will still be produced, but because the beam will stop at its intended range (which is a function of input energy), there may not be an exit spot.

In this case of an ion beam of lower energy that stops within the imaging cone, the coordinates of the beam may be derived using the entry spot location (501) and centroid $X_1Y_1Z_1$ (503) on the imaging cone (505) along with the path of the beam θ (theta) within the plastic scintillator.

Figure 5:
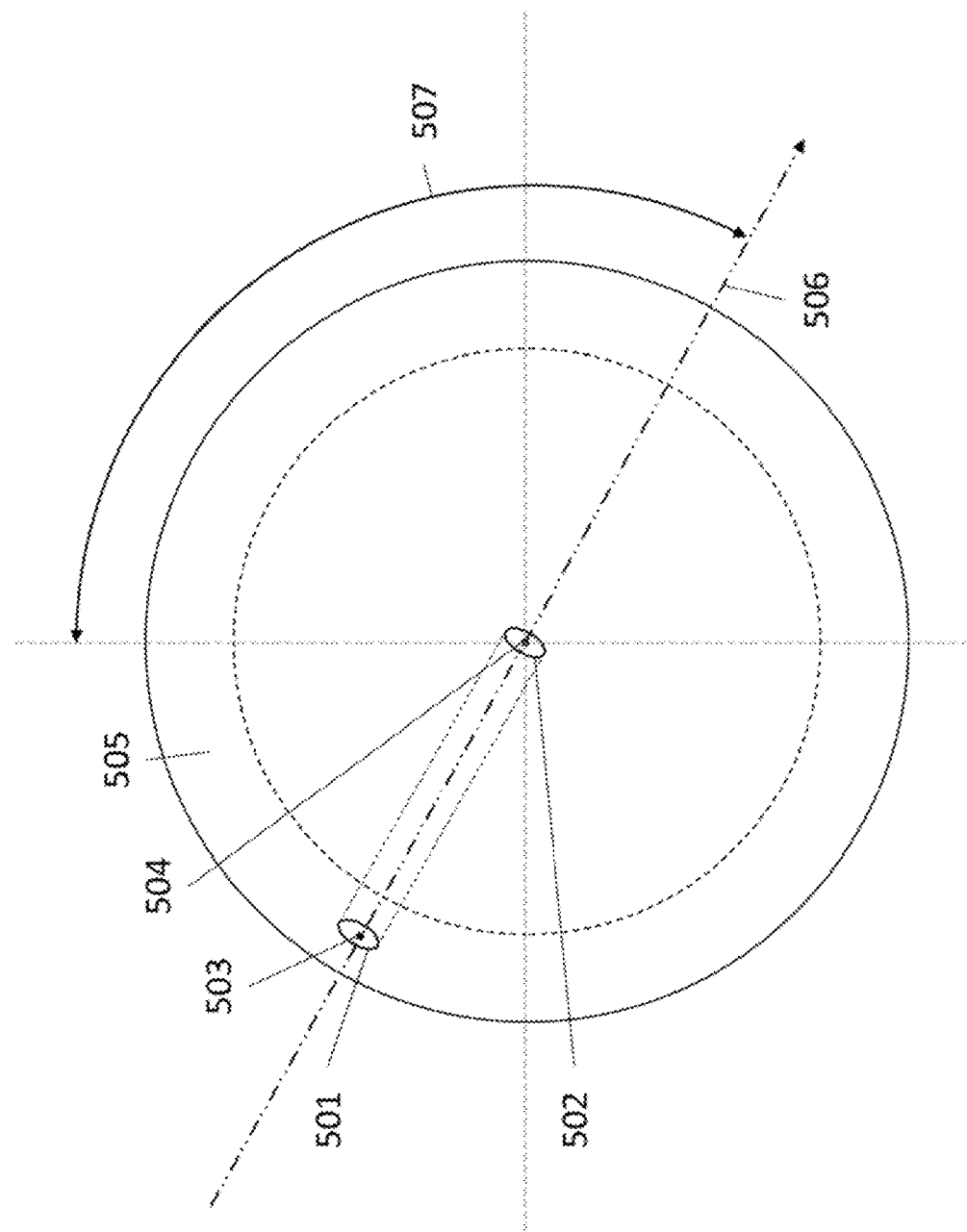
FIG. 5 is an explanatory diagram illustrating aspects of beam characterization.

As shown in FIG. 5, the beam ends within the plastic scintillator at the Bragg peak which is the brightest location of the beam within the plastic scintillator. The centroid location of the Bragg peak (502) is identified by centroid coordinates $X_2Y_2Z_2$ of a spatial location 504 which, along with the entry spot $X_1Y_1Z_1$ centroid (503), allows an angle θ (507) of the beam path 506 to be determined.

Every beam can be described by an XYZ location plus the angles θ and φ. For the case of an ion beam stopping within the scintillator plastic medium, φ will be assumed to be 90 degrees for the most common use case, which is gantry-based ion-beam delivery. (That is, the beam is assumed to enter the hodoscope normal to the surface of the hodoscope.) The XYZ location is called the isofocus and is defined as the closest point of approach of the beam path vector to the center axis of the imaging cone. The θ and isofocus of the ion beam can be calculated using centroids $X_1Y_1Z_1$ and $X_2Y_2Z_2$ assuming $\phi=90$ degrees.

Figure 6:
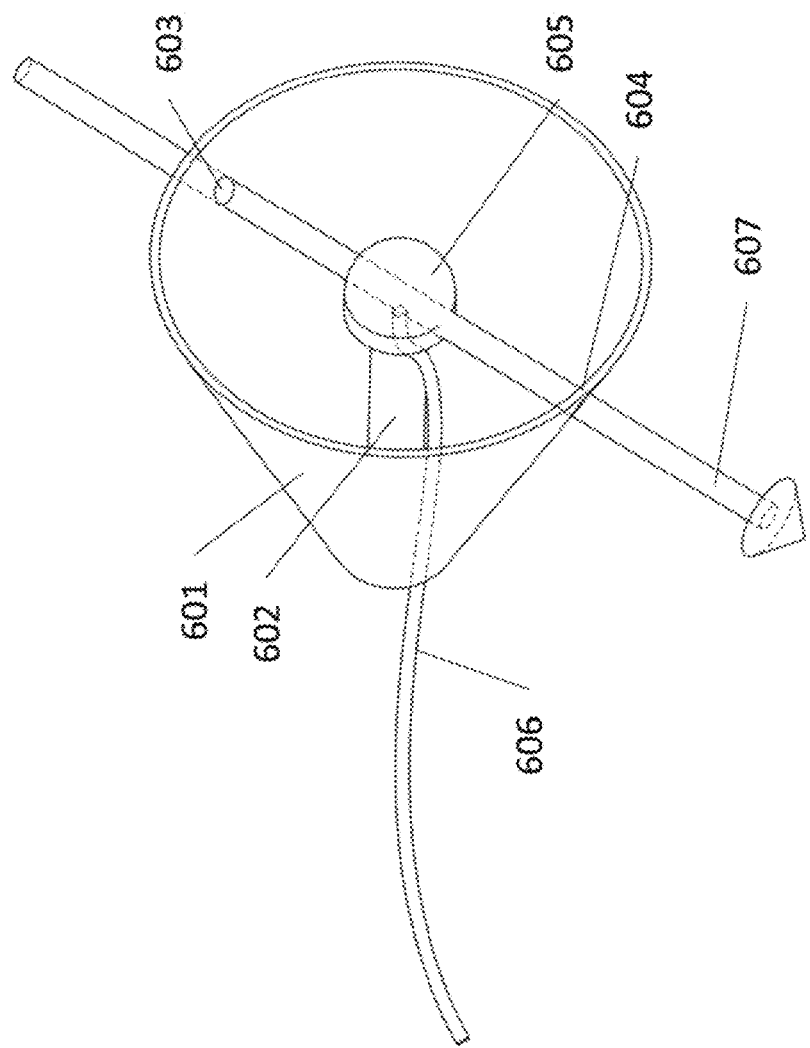
FIG. 6 is a diagram of a hodoscope provided with a post that holds a traditional radiation detector capable of measuring dose ("dose post"). The post is positioned such that it does not interfere with the operation of the hodoscope.

Traditional radiation dosimeters such as ion chambers can be used in conjunction with the hodoscope if they are placed within a holder 605 ("dose post") at the center of the imaging cone in a fashion that does not obstruct the view of a camera (not shown) of the imaging cone scintillator. The dose post holder contains typically 15 mm of plastic around the ion chamber for accurate measurements of the radiation at the center of the cone by the electrometer. In FIG. 6 the cable 606 connects the ion chamber within the dose post to an electrometer outside of the imaging cone. The hodoscope software measures the bright entry and exit spot positions on the imaging cone. Since the dose post is dark within the imaging cone, the spot location measurements of the spots are not affected.

In this fashion, the relative 3D dosimetry provided by the camera and imaging cone system can be directly correlated to an absolute dose as measured by the ion chamber, and any fluctuations in the camera electronics can be compensated for by the ion chamber measurement which is used as a reference value.

In one embodiment, an ion chamber is placed in the dose post. Other dose measurement devices may also be placed in the dose post instead of the ion chamber, including, for example, radiation diodes, MOSFETS, diamond detectors, film, Presage gel dosimeters, scintillator dosimeters, etc.

Figure 7:
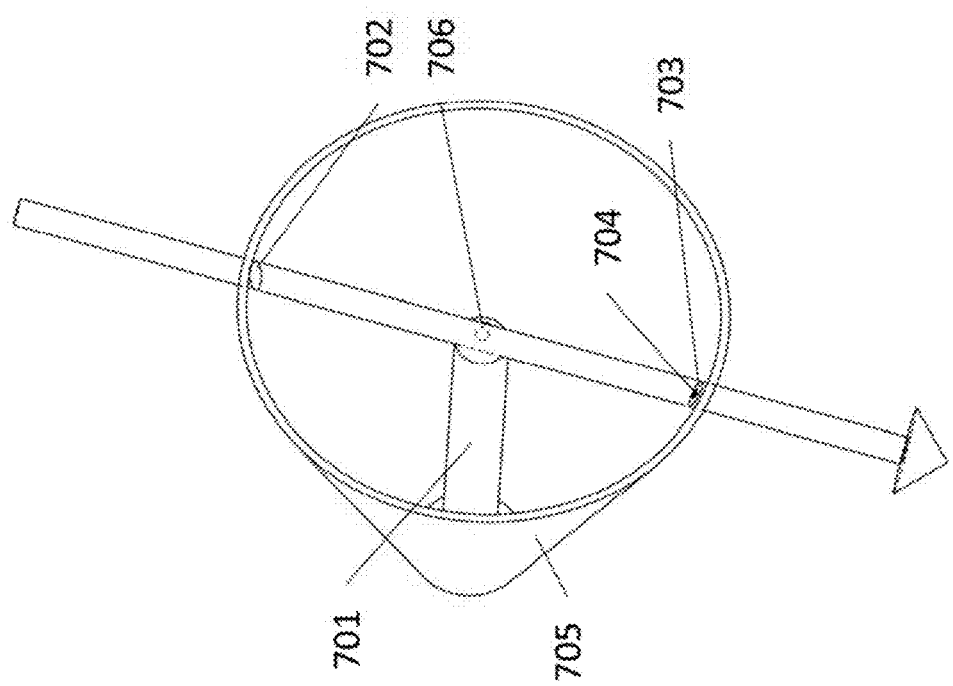
FIG. 7 is a diagram of a hodoscope provided with a fiducial element mounted on a post at the center of the imaging cone.

Referring to FIG. 7, a hodoscope is provided with one or more high density (high-Z) fiducial elements mounted along the center axis of the imaging cone 705. In the illustrated embodiment, a single BB 706 of tungsten is mounted at the end of a low-Z (e.g., plastic) rod 701. The BB may be a sphere of about 2.5 mm in diameter, for example. The X-ray/ion-beam system may use the fiducial(s) for targeting via X-ray or CT imaging techniques. The operation of the hodoscope still requires measurement of the entry 702 and exit 703 spots. Depending on the placement of the radiation beam, the single BB 706 forms a pattern within the exit spot 703. For x-rays this pattern can be likened to a "shadow" while for proton and heavy ion beams the pattern represents the dispersion of the particles from their original path. The location and shape of this pattern (or group of patterns) within the exit beam spot 703 may be used as a gauge of the targeting accuracy of the X-ray or ion beam delivery system.

It will be appreciated by those skilled in the art that the present invention may be embodied in other specific forms without departing the spirit or essential character thereof. The foregoing description is therefore understood in all respects to be illustrative and not restrictive. The scope of the invention is indicated by the appended claims, not the foregoing description, and all changes that come with the meaning and range of equivalents thereof are intended to be embraced therein.

What is claimed is:

1. A hodoscope dosimeter comprising a tapered scintillator volume that flashes light in at least two places when struck by an ionizing radiation beam from a stereotactic radiosurgery system, a camera that records an image of said light, and a computer that calculates location coordinates of said beam and that also calculates a profile of said beam, including its width and intensity; wherein the tapered scintillator volume is filled at least in part with a tissue equivalent plastic medium to form a plastic scintillator.

2. The hodoscope dosimeter of claim 1 wherein the plastic scintillator is a PVT (polyvinyltoulene) plastic scintillator.

3. The hodoscope dosimeter of claim 2, wherein the plastic medium is Bicron BC-412.

4. The hodoscope of claim 1, wherein the tissue equivalent plastic medium is cylindrical.

5. The hodoscope of claim 1, wherein the tapered scintillator volume is surrounded by tissue equivalent non-scintillator plastic.

6. The hodoscope of claim 1, comprising a hollow cylindrical housing situated along a center axis of the hodoscope.

7. The hodoscope of claim 6, comprising, within the hollow cylindrical housing, at least one of: an ion chamber, a radiation diode, a MOSFET, a diamond detector, film, a Presage gel, a Bang gel, and a scintillator dosimeter.

8. The hodoscope of claim 6, comprising, within the hollow cylindrical housing, electronic dosimeters positioned such that wiring for the electronic dosimeters exits along the center axis so that it does not interfere with an optical path associated with the hodoscope.

9. The hodoscope of claim 1, comprising at least one fiducial element situated along a center axis of the hodoscope.

10. The hodoscope of claim 9, wherein the fiducial element comprises a dense metallic body.

11. The hodoscope of claim 9, wherein the fiducial element is supported on an elongated cylindrical rod configured to be removed through an access hole at the end of the hodoscope opposite the camera.

12. A dosimetry method performed with respect to a radiation beam, the method comprising:
    receiving the radiation beam upon a tapered surface encircling a volume and having a scintillating layer applied thereto;
    receiving the radiation beam within a scintillating material contained by the volume and filling at least a majority of the volume; and
    capturing an image of a path of the radiation beam, including a path of the radiation beam within the volume.

13. The method of claim 12, comprising measuring a characteristic of the radiation beam using an electronic dosimeter situated within the volume.

14. The method of claim 12, comprising:
    the radiation beam interacting with a fiducial element situated within the volume;
    imaging a light pattern produced by the interacting of the radiation beam and the fiducial element; and
    evaluating a targeting accuracy of the radiation beam using the light pattern.

15. The method of claim 12, comprising the radiation beam interacting with a removable fiducial element situated within the volume to allow for comparison of light pattern measurements with and without the element.

* * * * *